United States Patent
Lai et al.

(10) Patent No.: US 8,883,095 B2
(45) Date of Patent: Nov. 11, 2014

(54) ANALYSIS CARTRIDGE AND ANALYSIS SYSTEM THEREOF

(71) Applicant: Lite-On IT Corporation, Taipei (TW)

(72) Inventors: Cheng-Chang Lai, Hsinchu (TW);
Fu-Chun Huang, Hsinchu (TW);
Yuh-Jiuan Lin, Hsinchu (TW);
Timothy Z. Liu, Hsinchu (TW)

(73) Assignee: Lite-On Technology Corporation, Taipei (TW)

(*) Notice: Subject to any disclaimer, the term of this patent is extended or adjusted under 35 U.S.C. 154(b) by 123 days.

(21) Appl. No.: 13/740,816

(22) Filed: Jan. 14, 2013

(65) Prior Publication Data

US 2013/0309133 A1 Nov. 21, 2013

(30) Foreign Application Priority Data

May 21, 2012 (CN) .......................... 2012 1 0157842

(51) Int. Cl.
*B01L 3/00* (2006.01)
*G01N 33/00* (2006.01)
*G01N 35/00* (2006.01)
*G01N 35/10* (2006.01)
*G01N 35/04* (2006.01)

(52) U.S. Cl.
CPC .......... *G01N 33/00* (2013.01); *B01L 2300/0806* (2013.01); *B01L 2400/0655* (2013.01); *G01N 2035/1032* (2013.01); *G01N 2035/0449* (2013.01); *B01L 3/502738* (2013.01); *B01L 2200/16* (2013.01); *B01L 3/508* (2013.01); *G01N 35/00069* (2013.01); *B01L 2300/0864* (2013.01); *G01N 2035/0405* (2013.01); *B01L 2400/0409* (2013.01)
USPC ............ 422/554; 422/66.1; 422/72; 422/506; 422/548; 422/559; 422/561; 435/287.3; 435/287.6; 435/288.2

(58) Field of Classification Search
None
See application file for complete search history.

(56) References Cited

U.S. PATENT DOCUMENTS

| 5,304,348 | A | 4/1994 | Burd et al. |
| 5,457,053 | A | 10/1995 | Burd et al. |
| 2008/0268529 | A1* | 10/2008 | Furusato et al. ............ 435/289.1 |
| 2010/0281961 | A1* | 11/2010 | Saiki et al. ................... 73/64.56 |

* cited by examiner

*Primary Examiner* — Jill Warden
*Assistant Examiner* — Timothy G Kingan
(74) *Attorney, Agent, or Firm* — Rabin & Berdo, P.C.

(57) ABSTRACT

An analysis cartridge and an analysis system thereof are disclosed. The analysis cartridge comprises a cartridge body, a liquid storage box and a sealing film. The cartridge body has an accommodation portion. The liquid storage box is disposed within the accommodation portion and has a liquid storage tank and a pillar receiving hole. The sealing film covers the pillar receiving hole and seals an opening of the liquid storage tank.

15 Claims, 4 Drawing Sheets

US 8,883,095 B2

ANALYSIS CARTRIDGE AND ANALYSIS SYSTEM THEREOF

This application claims the benefit of People's Republic of China application Serial No. 201210157842.9, filed May 21, 2012, the subject matter of which is incorporated herein by reference.

BACKGROUND OF THE INVENTION

1. Field of the Invention

The invention relates in general to an analysis cartridge and an analysis system thereof, and more particularly to the design of a sealing film of an analysis cartridge and an analysis system thereof.

2. Description of the Related Art

The in vitro diagnostic testing process comprises a following operation sequence: (1) a test specimen is infused; (2) the test specimen is diluted; (3) the test specimen is mixed with a reagent; (4) an optical signal is measured. The main purpose of diluting the test specimen is for reducing the disruptor and increasing the volume of the specimen so that a multi-objective test can be performed on a tiny quantity of test specimen. Therefore, the diluent will be mixed with the test specimen according to a particular proportion.

Of the products currently available in the market, a diluent box pre-filled with a diluent is packaged in an analysis cartridge. After the analysis cartridge is loaded into an analyzer, the mechanism design of the analyzer opens an opening of the diluent box for allowing the diluent pre-filled in the diluent box to flow out the diluent box to be mixed with the test specimen so that the test specimen can be diluted.

However, the procedure of opening the diluent box requires a complicated mechanism design, which not only increases the operation complexity, but further increases the size and weight of the analyzer.

SUMMARY OF THE INVENTION

The invention is directed to an analysis cartridge and an analysis system thereof, which dispenses with a mechanism of opening a seal film of a liquid storage box so as to effectively reduce cost and increase market competiveness.

According to one embodiment of the present invention, an analysis cartridge is disclosed. The analysis cartridge comprises a cartridge body, a liquid storage box and a sealing film. The cartridge body has an accommodation portion. The liquid storage box is disposed within the accommodation portion and has a liquid storage tank and a pillar receiving hole. The sealing film covers the pillar receiving hole and seals an opening of the liquid storage tank.

According to another embodiment of the present invention, an analysis system is disclosed. The analysis system comprises an analysis cartridge and an analyzer. The analysis cartridge comprises a cartridge body, a liquid storage box and a sealing film. The analysis cartridge has an accommodation portion. The liquid storage box is disposed within the accommodation portion and has a liquid storage tank and a pillar receiving hole. The sealing film covers the pillar receiving hole and seals an opening of the liquid storage tank. The analyzer comprises a supporting base and a protrudent pillar, wherein the protrudent pillar is disposed on the supporting base. During operating the analysis cartridge on the supporting base, the protrudent pillar pushes the sealing film into the pillar receiving hole and pulls the sealing film sealing the liquid storage tank to expose the opening of the liquid storage tank.

According to another embodiment of the present invention, an analysis cartridge is disclosed. The analysis cartridge comprises a cartridge body, a liquid storage box and a sealing film. The cartridge body has an accommodation portion. The liquid storage box is disposed within the accommodation portion and has a liquid storage tank and a pillar receiving hole. The sealing film is for sealing an opening of the liquid storage tank and has two terminals, wherein two terminals of the sealing film are fixed on different sides of the liquid storage box.

The above and other aspects of the invention will become better understood with regard to the following detailed description of the preferred but non-limiting embodiment(s). The following description is made with reference to the accompanying drawings.

DETAILED DESCRIPTION OF THE INVENTION

Figure 1:
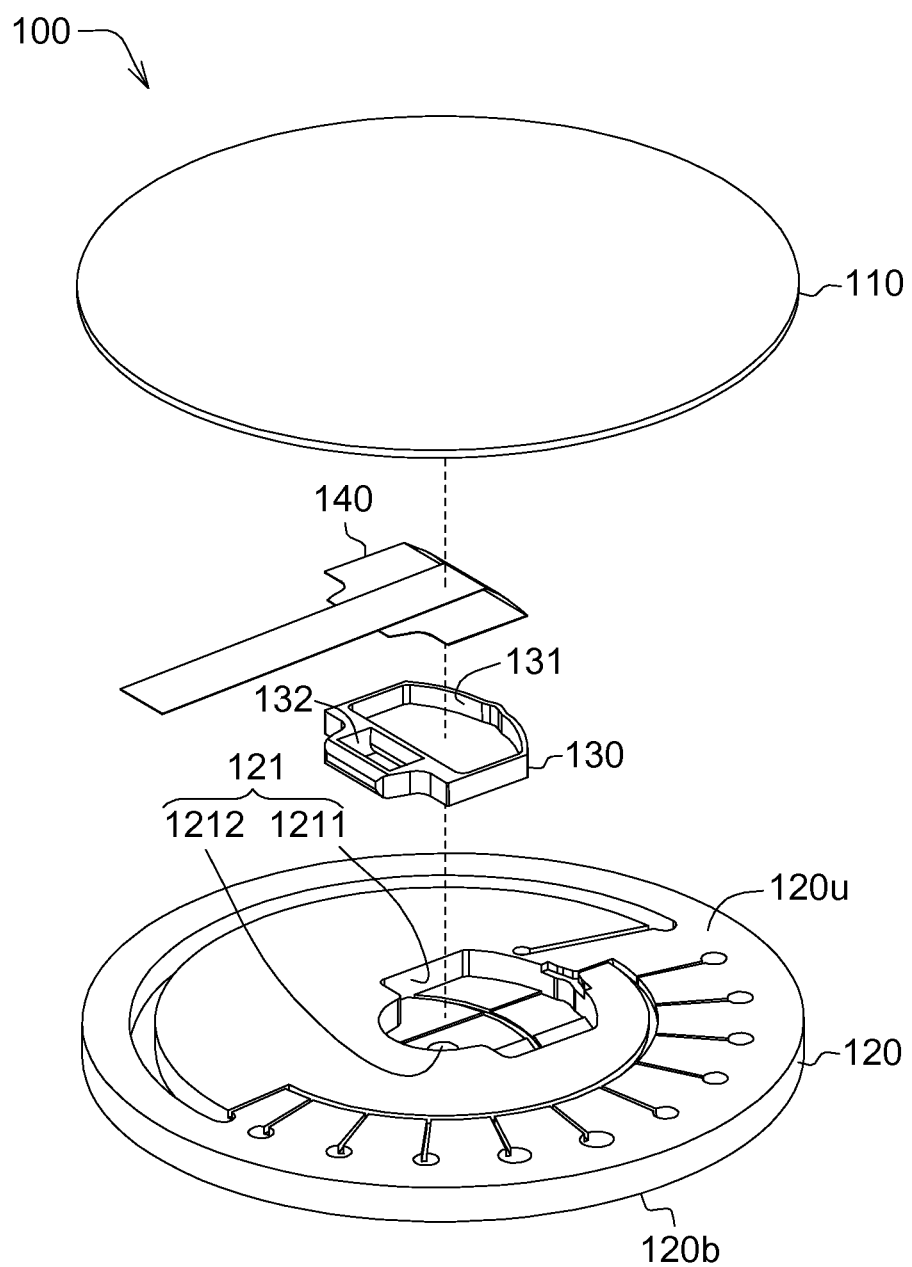
FIG. 1 shows an explosion diagram of an analysis cartridge according to an embodiment of the invention.

Referring to FIG. 1, an explosion diagram of an analysis cartridge according to an embodiment of the invention is shown. The analysis cartridge 100 comprises a cover 110, a cartridge body 120, a liquid storage box 130 and a sealing film 140.

The cover 110 covers a first side 120u of the cartridge body 120. The cover 110 may be formed by a high polymer such as polypropylene (PP) or polymethylmethacrylate (PMMA). Under such design, the cover 110 may be bonded to the cartridge body 120 by the hot melting method or the ultrasound bonding technology. Alternatively, the cover 110 may be formed by an adhesive material such as an adhesive tape. Under such design, the cover 110 may be adhered to the cartridge body 120.

The cartridge body 120 has an accommodation portion 121, and a first side 120u and a second side 120b opposite to the first side 120u. The accommodation portion 121 extends towards the second side 120b from the first side 120u. In the present embodiment, the accommodation portion 121 is a recess. The cartridge body 120 may be formed by plastics such as polypropylene.

Figure 2:
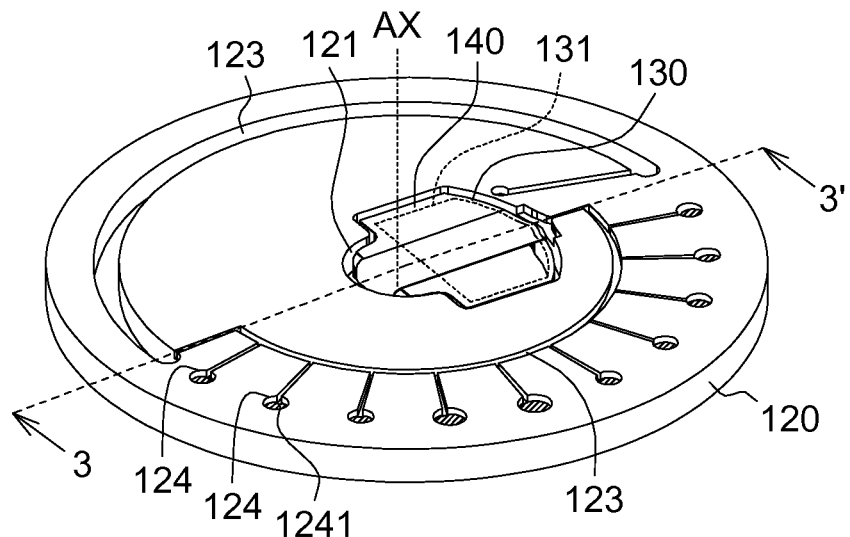
FIG. 2 shows an assembly diagram of a cartridge body, a liquid storage box and a sealing film of FIG. 1.

Referring to FIG. 2, an assembly diagram of a cartridge body, a liquid storage box and a sealing film of FIG. 1 is shown. The accommodation portion 121 may contain the liquid storage box 130. When analysis is not performed, an opening of a liquid storage tank 131 of the liquid storage box 130 is sealed by the sealing film 140 to avoid the diluent L (FIG. 3) inside the liquid storage box 130 flowing out via the liquid storage tank 131.

The cartridge body 120 has a liquid channel 123 and at least one reaction chamber 124. The liquid channel 123 interconnects the reaction chamber 124 with the opening of the liquid storage tank 131 of the liquid storage box 130, such that the diluent L inside the liquid storage box 130 may flow to the reaction chamber 124 via the opening of the liquid storage tank 131 and the liquid channel 123 to react with the reactive substance 1241 stored in the reaction chamber 124.

Figure 3:
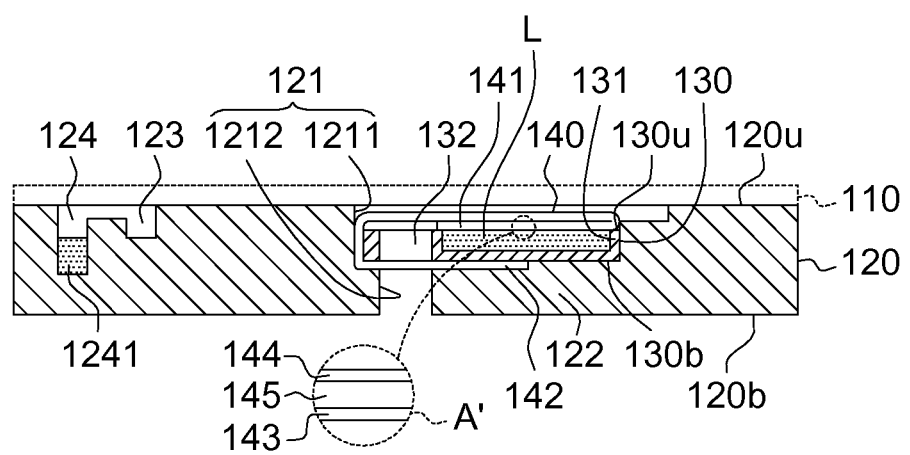
FIG. 3 shows a cross-sectional view along a direction 3-3' of FIG. 2.

Referring to FIG. 3, a cross-sectional view along a direction 3-3' of FIG. 2 is shown. The liquid storage box 130 is disposed within the accommodation portion 121 and has a liquid storage tank 131, a pillar receiving hole 132, a first side 130u and a second side 130b opposite to the first side 130u. The liquid storage tank 131 extends towards the second side 130b from the first side 130u of the liquid storage box 130. The pillar receiving hole 132 extends towards the first side 130u from the second side 130b of the liquid storage box 130. In other words, the opening of the liquid storage tank 131 and the opening of the pillar receiving hole 132 face different sides.

The accommodation portion 121 comprises a recess 1211 and a through hole 1212. The recess 1211 extends a distance towards the second side 120b from the first side 120u of the cartridge body 120, wherein the distance is smaller than a thickness of the cartridge body 120 so that a recess bottom 122 is formed and the liquid storage box 130 is disposed on the recess bottom 122. The through hole 1212 is formed on the recess bottom 122 of the recess 1211 and corresponds to the pillar receiving hole 132 of the liquid storage box 130.

As indicated in FIG. 3, the sealing film 140 is bended after one terminal 141 of the sealing film 140 is fixed on the first side 130u of the liquid storage box 130 and seals the opening of the liquid storage tank 131. Another terminal 142 of the sealing film 140 is fixed on the second side 130b of the liquid storage box 130. That is, the sealing film 140 is bended for covering the opening of the pillar receiving hole 132 after one terminal 141 of the sealing film 140 seals the opening of the liquid storage tank 131, while another terminal of the sealing film 140 may be fixed on a bottom of the liquid storage box 130. In other words, two terminals of the sealing film 140 are fixed on different sides of the liquid storage box 130.

As indicated in an enlargement diagram of a portion A' of FIG. 3, the sealing film 140 is such as a multi-layer structure. For example, the sealing film 140 comprises a bonding layer 143, a metal layer 144 and an adhesive layer 145.

The bonding layer 143 seals the liquid storage tank 131, and the adhesive layer 145 is formed between the bonding layer 143 and the metal layer 144 for bonding the bonding layer 143 to the metal layer 144. In an embodiment, the bonding layer 143 and the cartridge body 120 may be formed by the same material such as polypropylene (PP) or polyethylene terephthalate (PET). During the hot melt process, after the bonding layer 153 reaches the glass transition temperature, the bonding layer 143 may be bonded to the liquid storage box 130.

The metal layer 144 is formed by a metal having superior thermal conductivity such as aluminum or other metal. Due to the superior thermal conductivity, the metal layer 144, without contacting the sealing film 140, may transmit the heat to the bonding layer 143 via the metal layer 144 for heating the bonding layer 143.

Figure 4:
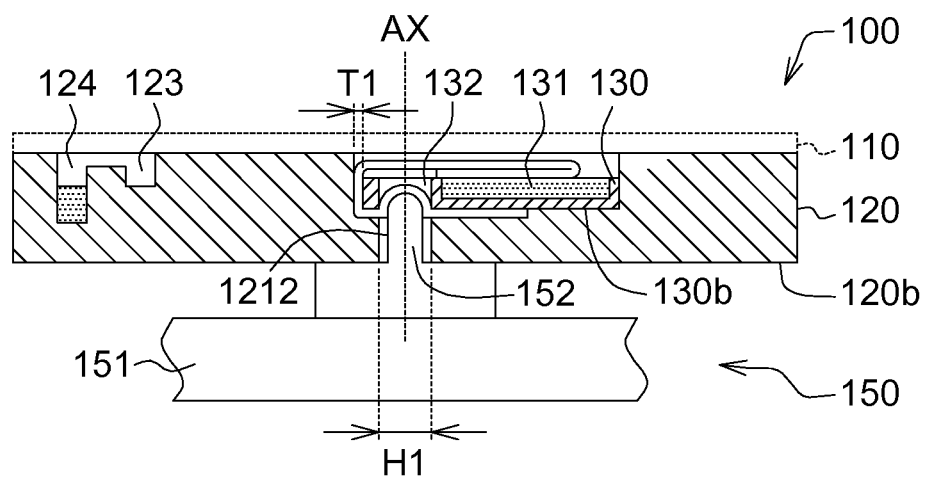
FIG. 4 shows a schematic diagram of loading an analysis cartridge of FIG. 3 to an analyzer.

Referring to FIG. 4, a schematic diagram of loading an analysis cartridge of FIG. 3 to an analyzer is shown. The analyzer 150 comprises a supporting base 151 and a protrudent pillar 152, wherein the protrudent pillar 152 is disposed on the supporting base 151. When analysis is performed, the operator aligns the through hole 1212 of the analysis cartridge 100 with the protrudent pillar 152 of the analyzer 150, and disposes the analysis cartridge 100 on the supporting base 151 of the analyzer 150. During disposing the analysis cartridge 100 on the supporting base 151, the protrudent pillar 152 pushes the sealing film 140 into the pillar receiving hole 132 and pulls the sealing film 140 sealing the liquid storage tank 131 to expose the liquid storage tank 131. Then, the analyzer 150 drives the analysis cartridge 100 to rotate around an axis AX, so that the diluent L stored in the liquid storage box 130 is driven by the centrifugal force to flow to the liquid channel 123 through the exposed liquid storage tank 131. In addition, the axis AX is such as the center of the analysis cartridge 100.

When the analysis cartridge 100 is disposed on the supporting base 151 of the analyzer 150, the second side 130b of the liquid storage box 130 faces the inside of the accommodation portion 121. During the process in which the analyzer 150 drives the analysis cartridge 100 to rotate around an axis AX, the centrifugal force drives the diluent L inside the liquid storage box 130 to flow to the reaction chamber 124 via the exposed liquid storage tank 131 and the liquid channel 123, such that the diluent L reacts with the reactive substance 1241 inside the reaction chamber 124. In the present embodiment, the reaction chamber 124 is a blind hole.

Figure 5:
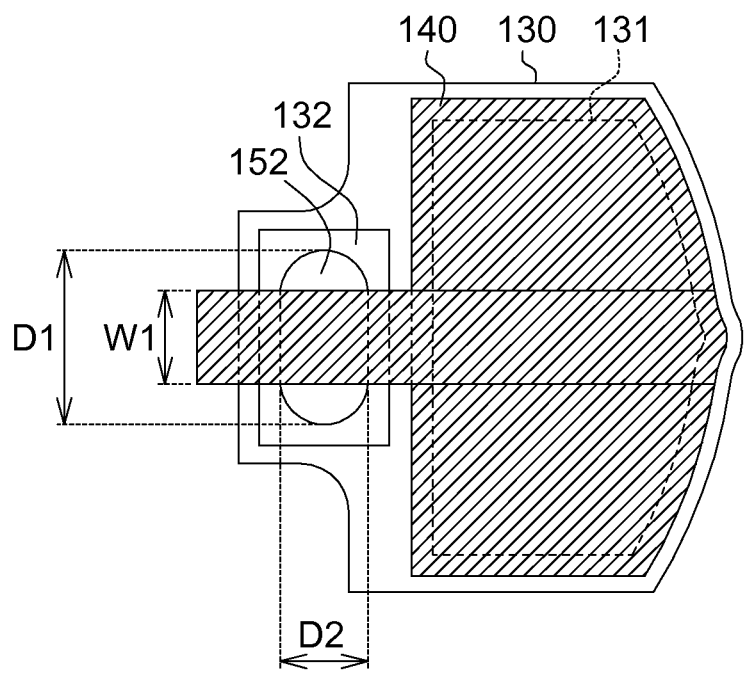
FIG. 5 shows a top view of a protrudent pillar, a liquid storage box and a sealing film of FIG. 4.

Referring to FIG. 5, a top view of a protrudent pillar, a liquid storage box and a sealing film of FIG. 4 is shown. The sealing film 140 has a strip portion whose width W1 is smaller than an inner diameter H1 of the pillar receiving hole 132. The outer diameter D1 of the protrudent pillar 152 ranges between the inner diameter H1 of the pillar receiving hole 122 and the width W1 of the sealing film 140. In an embodiment, the sum of another outer diameter D2 of the protrudent pillar 152 and two times of the thickness T1 of the sealing film 140 (FIG. 4) is smaller than or equal to the inner diameter H1 of the pillar receiving hole 132 (FIG. 4) for allowing the protrudent pillar 152 to enter the pillar receiving hole 132 easily.

Figure 6:
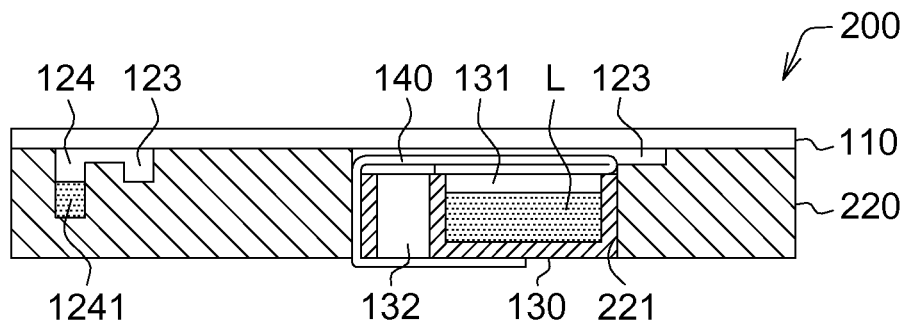
FIG. 6 shows a cross-sectional view of an analysis cartridge according to another embodiment of the invention.

Referring to FIG. 6, a cross-sectional view of an analysis cartridge according to another embodiment of the invention is shown. The analysis cartridge 200 comprises a cover 110, a cartridge body 220, a liquid storage box 130 and a sealing film 140.

The cartridge body 220 has an accommodation portion 221, which extends to the second side 120b from the first side 120u of the cartridge body 220. That is, the accommodation portion 221 is a through hole via which the liquid storage box 130 disposed within the accommodation portion 221 is exposed from the first side 120u and the second side 120b of the cartridge body. The liquid storage box 130 is tightly engaged within the accommodation portion 221.

Figure 7:
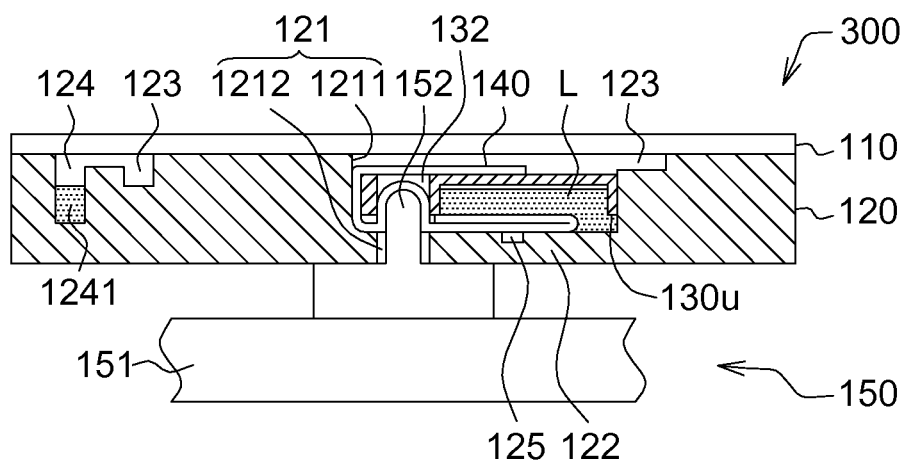
FIG. 7 shows a cross-sectional view of an analysis cartridge according to another embodiment of the invention.

Referring to FIG. 7, a cross-sectional view of an analysis cartridge according to another embodiment of the invention is shown. The analysis cartridge 300 comprises a cover 110, a cartridge body 120, a liquid storage box 130 and a sealing film 140.

The cartridge body 120 has an accommodation portion 121, which extends a distance towards the second side 120b from the first side 120u. The distance is smaller than a thickness of the cartridge body 120 so that a recess bottom 122 is formed, and the liquid storage box 130 is disposed on the recess bottom 122.

The cartridge body 120 has a recess channel 125, a liquid channel 123 and a reaction chamber 124. The liquid channel 123 interconnects the reaction chamber 124 with the liquid storage tank 131 (FIG. 2), and the recess channel 125 is formed on the recess bottom 122 and located between the liquid channel 123 and the pillar receiving hole 132 of the liquid storage box 130. In this embodiment, the opening of the liquid storage tank 131 and the opening of the pillar receiving hole 132 face the same side.

After the analysis cartridge 300 is disposed on the analyzer 150, the protrudent pillar 152 pushes the sealing film 140 into the pillar receiving hole 132 and pulls the sealing film 140 sealing the liquid storage tank 131 to expose the liquid storage tank 131. In the present embodiment, the first side 130u of the liquid storage box 130 faces the inside of the accommodation portion 121. After the liquid storage tank 131 is exposed, the diluent L stored in the liquid storage tank 131 flows out from the liquid storage tank 131. The recess channel 125 may accommodate the overflown diluent L to avoid the diluent L flowing out the cartridge body 120 via the through hole 1212 of the accommodation portion 121.

While the invention has been described by way of example and in terms of the preferred embodiment(s), it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. An analysis cartridge, comprising:
   a cartridge body having an accommodation portion;
   a liquid storage box disposed within the accommodation portion and having a liquid storage tank and a pillar receiving hole; and
   a sealing film covering the pillar receiving hole at a first level corresponding to an upper end of the tank and at a lower, second level vertically spaced from the first level, and
   sealing an opening of the liquid storage tank.

2. The analysis cartridge according to claim 1, wherein the accommodation portion comprises a through hole corresponding to the pillar receiving hole of the liquid storage box.

3. The analysis cartridge according to claim 1, wherein a bottom of the liquid storage box faces the inside of the accommodation portion.

4. The analysis cartridge according to claim 1, wherein an opening of the liquid storage tank of the liquid storage box faces the inside of the accommodation portion.

5. The analysis cartridge according to claim 1, wherein the cartridge body has a liquid channel and a reaction chamber, and the liquid channel interconnects the reaction chamber with the accommodation portion of the cartridge body.

6. The analysis cartridge according to claim 1, wherein a terminal of the sealing film is fixed on an opening of the liquid storage tank of the liquid storage box while another terminal of the sealing film is fixed on the bottom of the liquid storage box.

7. The analysis cartridge according to claim 1, wherein the sealing film has two terminals, and the terminals of the sealing film are fixed on the same side or on the opposite sides of the said liquid storage box.

8. The analysis cartridge according to claim 1, wherein a width of the sealing film is smaller than an inner diameter of the pillar receiving hole.

9. An analysis system, comprising:
   an analysis cartridge, comprising:
      a cartridge body having an accommodation portion;
      a liquid storage box disposed within the accommodation portion and having a liquid storage tank and a pillar receiving hole; and
      a sealing film covering the pillar receiving hole at a first level corresponding to an upper end of the tank and at a lower, second level vertically spaced from the first level, and sealing an opening of the liquid storage tank; and
   an analyzer comprising a supporting base and a protrudent pillar disposed on the supporting base;
   wherein, during operating the analysis cartridge on the supporting base, the protrudent pillar pushes the sealing film into the pillar receiving hole and pulls the sealing film to expose the opening of the liquid storage tank.

10. The analysis system according to claim 9, wherein a width of the sealing film is smaller than an inner diameter of the pillar receiving hole, and an outer diameter of the protrudent pillar ranges between the inner diameter of the pillar receiving hole and the width of the sealing film.

11. The analysis system according to claim 9, wherein the sum of the outer diameter of the protrudent pillar and two times of the thickness of the sealing film is smaller than or equal to the inner diameter of the pillar receiving hole.

12. The analysis system according to claim 9, wherein the accommodation portion comprises a through hole corresponding to the pillar receiving hole of the liquid storage box.

13. The analysis system according to claim 9, wherein a bottom of the liquid storage box faces the inside of the accommodation portion.

14. The analysis system according to claim 9, wherein an opening of the liquid storage tank of the liquid storage box faces the inside of the accommodation portion.

15. The analysis system according to claim 9, wherein a terminal of the sealing film is fixed on an opening of the liquid storage tank of the liquid storage box while another terminal of the sealing film is fixed on the bottom of the liquid storage box.

* * * * *